United States Patent [19]
Colin

[11] Patent Number: 4,715,988
[45] Date of Patent: Dec. 29, 1987

[54] STANDARD FOR ANALYSIS

[75] Inventor: David Colin, South Glamorgan, Wales

[73] Assignee: Amersham International plc., Buckinghamshire, England

[21] Appl. No.: 699,395

[22] Filed: Feb. 7, 1985

[30] Foreign Application Priority Data

Feb. 7, 1984 [GB] United Kingdom ............ 8403128

[51] Int. Cl.⁴ .................. C09F 7/00; G01N 31/00
[52] U.S. Cl. .................... 252/408.1; 436/8; 427/5
[58] Field of Search ............ 252/408.1; 424/33–37; 604/890; 427/151, 152, 333, 338, 5

[56] References Cited

U.S. PATENT DOCUMENTS

| | | |
|---|---|---|
| 4,053,433 | 10/1977 | Lee ............................ 252/408.1 |
| 4,062,799 | 12/1977 | Matsukowa et al. ......... 252/408.1 |
| 4,138,390 | 2/1979 | Emmoss et al. ............ 252/408.1 |
| 4,152,271 | 5/1979 | Eisenberg .................. 252/408.1 |
| 4,350,414 | 9/1982 | Takahashi et al. .......... 252/408.1 |
| 4,431,766 | 2/1984 | Christie et al. ............. 252/408.1 |
| 4,507,233 | 3/1985 | Saito et al. ................. 252/408.1 |

Primary Examiner—Deborah L. Kyle
Assistant Examiner—T. J. Wallen
Attorney, Agent, or Firm—Wenderoth, Lind & Ponack

[57] ABSTRACT

A block of polymeric material 12 comprises label layers 14 and interposed non-label layers 16, each label layer containing a different known concentration of a label material. The block can be sliced by a microtome 18 into thin section each of which is useful as a standard for analysis e.g. in autoradiography. Preferred label materials are radioactive isotopes e.g. 3-H and 14-C; other label materials include metals and fluorescent materials.

14 Claims, 1 Drawing Figure

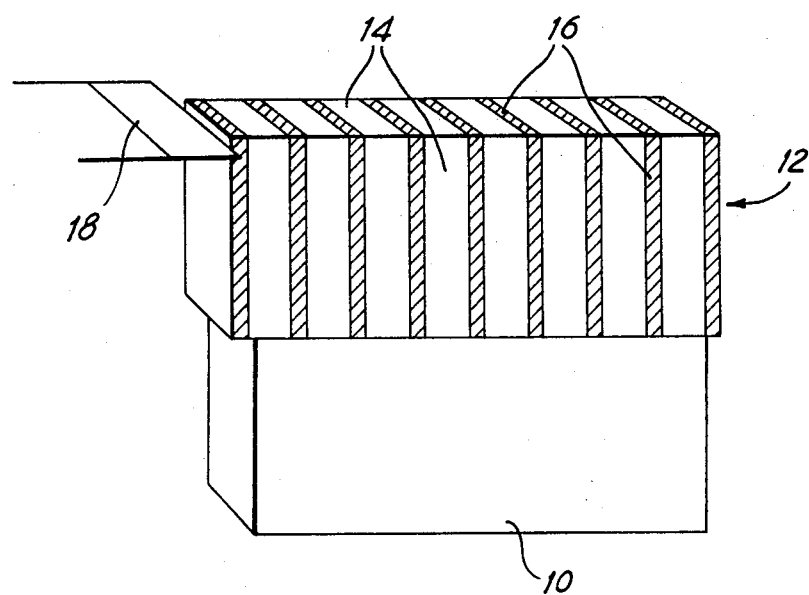

STANDARD FOR ANALYSIS

This invention relates to standards for analysis. The standard contains a label material, for example a fluorescent material, or a metal for x-ray microanalysis, or a radioactive isotope for autoradiography.

An autoradiograph is formed by placing a section, generally thin, suspected of containing radioactivity, adjacent a photographic emulsion, and leaving it in position for a suitable time, usually several days or weeks. On developing the emulsion, black or coloured spots or regions are observed in positions corresponding to the location of radioactivity in the sample. The density of colour increases with increasing radioactive concentration in the sample. Hence, the colour density can be used to determine the radioactive concentration of the sample, provided that there is also used a set of standards of known radioactive concentration.

In macroscopic autoradiography, after administration of a radioactively labelled compound, the animal or organ is frozen, sectioned using a microtome, and the section lifted off the microtome attached to sticky tape. These sections, usually 20 microns thick, are placed in contact with a sheet of a suitable detector, usually a special photographic film. It is usual to autoradiograph many sections simultaneously. After development of the film, the location and extent of blackening are measured using a densitometer or microdensitometer with an aperture which may be as low as 50 microns. Isotopes most frequently used are 14-C, 3-H, 125-I, 35-S, 32-P and 22-Na.

In microscopic autoradiography, microtome sections 0.5–5 microns thick are mounted on microscope slides, autoradiographed and stained. Three autoradiographic techniques are used. The microscope slide can be dipped into a photographic emulsion, or the section can be covered with an emulsion coated cover slip or prepared very thin film, or the slide can be laid face down on a sheet of autoradiographic film. The first two techniques enable the photographic emulsion to be kept in position on the slide to more closely relate morphological details to radioactivity particularly by silver grain counting. The third technique is particularly used where densitometric measurements are to be taken. Isotopes most frequently used are those which emit low energy electrons such as 3-H, 125-I, 55-Fe, 57-Co and 75-Se.

In all these techniques, the use of a set of standards with each section (or each set of sections) is required to avoid errors due to variations in film sensitivity, exposure time, development and stability after development. Standards are generally made up in the research worker's laboratory, e.g. by forming a series of solutions of a radioactively labelled compound at different dilutions, absorbing these on x-ray film, and mounting pieces of film for autoradiography alongside the sample sections. This is a time-consuming process. There is a need for standards which do not require extensive preparation.

Available on the market as reference sources are blocks of plastics materials containing in uniform dispersion a known concentration of a radioactive isotope or other label. By cutting a slice of desired thickness there is obtained a standard section to be placed alongside the sample section. But to provide a set of standards, several blocks of different activity would be needed, with a slice cut from each block. The resulting standard sections would be large and awkward to handle.

The present invention provides a block of polymeric material for the preparation of standards for analysis, the block including at least two label layers, each label layer being of uniform thickness and containing a known concentration of a label material uniformly distributed therein.

Non-label layers are preferably interposed between the label layers. The label layers are preferably substantially parallel and substantially flat. The user simply slices a layer of desired thickness from the block, cutting in a direction perpendicular to the plane of the parallel label layers, to obtain a standard section to be placed alongside the sample section. Alternatively, the manufacturer may slice the block up himself in order to use or sell the sections separately.

The nature of the label material is not critical, and various examples are given:

(a) Commercially available standards for X-ray analysis comprise organometallic compounds uniformly dispersed in polymer blocks. Slices are cut for use as standards; under a beam of electrons, the metal emits X-rays of characteristic wavelength, see "Physical Metallurgy for Engineers" by A. G. Guy, pages 84–86. Elemental standards for sodium, potassium and zinc are available at a variety of different concentrations, but only one element in a single concentration in each standard. X-ray fluorescence analysis similarly makes use of organometallic compounds in polymer blocks as standards, as described in "Advances in X-ray Analysis", Volume 20, pages 411–421 by T. G. Dzubay et al.

According to this invention, blocks can contain layers of different elements, for example Na, K, Zn, Ca, Fe, Co, Ni, Mg, Cu, Pb or V, and/or layers of different concentrations of the same element. Thus the multiple standards that have been required in the past can be replaced by a single standard.

(b) A standard according to this invention may comprise a polymeric block containing layers of different concentration of a fluorescent material, e.g. fluorescin, as the label material. An animal organ containing the fluorescent material can be frozen, and sections of known thickness cut from both the organ and the standard. (Alternatively the organ can be stained after sectioning by the Kuhar technique.) Excitation of the fluorescent material in both sections can then readily give a measure of the concentration of the material in the organ. See "Standardisation of Immunofluorescence" chapter 20 by J. S. Ploem.

(c) The use of standards according to the invention, in which the label material is a radioactive isotope, has been described above.

(d) The term "label material" is herein used to include reactive groups to which radioactive isotopes can be attached just prior to use. This option, which is described in more detail below, may be particularly useful with a short-lived radioactive isotope such as 125-I.

Preferably, each label layer contains a different concentration of label material. Preferably, the block contains more than 2, e.g. 3 to 20, label layers containing different known concentrations of radioactive isotope or other label material spanning the entire expected concentrations of different parts of the samples. It is possible, though not preferred, to have label layers of different thicknesses in one block. It is possible, to have label layers containing different labels in one block, this is likely to be particularly useful for X-ray microanalysis.

The nature of the polymeric material is not critical. As synthetic polymers, polyacrylates, polymethacrylates and epoxy resins are examples of suitable materials. It may be advantageous to use naturally occurring polymers or biopolymers including gelatin and the polysaccharides dextran and cellulose and derivatives such as cellulose acetate. A crosslinking agent is preferably included to prevent swelling in water and to ensure that the label material is securely held.

Techniques are known for making sheets of uniform thickness and containing a uniform distribution of a radioactive isotope or other label material. Reference sources of poly-(14-C)methyl methacrylate and of poly-(3-H)methyl methacrylate and of poly-(3-H)butyl methacrylate are available commercially in a range of specific activities per gram of polymer. Such materials can be used to make up the blocks of this invention. Other plastics materials, and the possibility of using other radioactive isotopes or other label materials, will readily occur to the skilled worker.

The block may be provided with a base of non-labelled material for clamping. This permits the whole of the active region to be sliced off for use as standard sections. The size of the block should preferably be such that the area of the section sliced off is similar to that of the samples under examination. This may typically be in the range of 0.001 cm$^2$ up to 10 cm$^2$, for use in electron microscopy and in whole body autoradiography respectively.

Reference is directed to the accompanying drawing which is a perspective view of one embodiment of the invention. The drawing shows a block of plastics material for autoradiography including a base 10 for clamping and an upper portion 12 composed of eight label layers 14, each of tritiated methacrylate of a different known specific activity, and interposed nonlabel layers 16 of non-radioactive coloured methacrylate. The length of the block (perpendicular to the planes of the layers) is 21 mm, and each layer measures 10 mm×3 mm in area. The label layers are each about 1.5 mm thick, and the interposed non-label layers about 1 mm thick. A microtome blade 18 is shown positioned to slice off a section 5 microns thick for use alongside a sample being autogradiographed.

The block was prepared as follows. First, each of the active layers was made separately using a mixture of 85 parts by volume of butyl methacrylate and 15 parts by volume of methyl methacrylate, each of these having been labelled to a known specific activity with 3-H, together with 1 part by volume of ethylene dimethacrylate as a cross-linking agent. The layers were formed at 1.5 mm thickness and polymerised by heating at 60° C. using 0.1%, by weight on the weight of the monomers, of azodibutyronitrile as a catalyst. Then the inactive layers were made using the same formulation, with a dye but without the radioactively labelled monomers, at a thickness of 1 mm. Then the layers were superimposed in the desired order, using a partly polymerised mixture of the same formulation as adhesive, held together by a clamp and heated to 60° C. so as to complete the polymerisation and form a slab 25 mm thick. This was cut, perpendicular to the plane of the layers, into slices 10 mm thick. Each slice was bonded using the same adhesive technique to a non-active slice of the same formulation and substantially the same dimensions. The resulting double slice was cut, perpendicular to the planes of the layers and of the previous cut, into blocks 3 mm thick, one of which is shown in the drawing.

The dye used for the non-active layers should be one which does not fluoresce. The end non-active layer adjacent the active layer having the highest (or alternatively the lowest) specific activity may be coloured differently from the others to act as a marker. If standards are provided containing different radioactive isotopes, the colours of the non-active layers may serve to indicate the nature of the isotope.

It is known that polymer labelled with a radio-isotope emits fewer beta particles than biological tissue labelled to the same radioactive concentration. This factor has been taken into account in deciding the radioactive concentrations (in microcuries per gram) in the active layers, as follows:

| Radioactive Concentrations | 3 | 12.3 | 19.2 | 33.5 | 55 | 75 | 92 | 110 |
|---|---|---|---|---|---|---|---|---|
| Tissue Equivalent Values | 1.3 | 4.9 | 7.8 | 12.3 | 18.8 | 24.5 | 28.8 | 33.0 |

Microtome sections prepared from this block have the following features:

(i) A multi-value standard strip of "infinite thickness", i.e. greater than 5 microns for tritium. ("Infinite thickness" for 14-C would be greater than 80 microns).

(ii) Available rapidly in large numbers at low cost.

(iii) Large enough for the image to be read easily by a microdensitometer, but small enough to fit on a microscope slide alongside a sample tissue section.

(iv) Of similar thickness to sample tissue sections (say not more than a few tens of microns thick).

(v) Tissue equivalent values of standards cover the range of radioactive concentration expected in tissue sections.

It will be apparent that other standards according to this invention can be prepared by techniques corresponding to those described above, merely using different label materials.

In one alternative embodiment, the label layers are formed of a liquid permeable plastics material (such as are commercially available) and contain, bound to the plastics matrix or trapped within it, different concentrations of a reactive compound. A block of plastics material containing at least two such label layers is formed. The block is sliced to give sections of suitable thickness which are then uniformly impregnated with a radioactive isotope, e.g. by immersion in a solution containing the radioactive isotope in a suitable chemical form. After the radioactive isotope has become bound to the plastics matrix or trapped within it, in a concentration corresponding to the concentration of the reactive compound, the section is washed and dried and is then ready for use.

This impregnation operation can be performed shortly prior to use of the section as an analysis standard, and this makes the option particularly valuable for radioactive isotopes having a short half-life. For example 125-I has a half-life of only 60 days, so that a whole block containing 125-I as the label material would have rather limited value unless it could be used up quickly.

I claim:

1. A block of polymeric material for the preparation of standards for analysis, the block including at least two label layers, each label layer being of uniform thickness and containing a known concentration of a label material uniformly distributed therein and different layers containing different concentrations of the label material.

2. The block as claimed in claim 1, wherein the label material is a radioactive isotope.

3. The block as claimed in claim 2, wherein the radioactive isotope is 3-H or 14-C.

4. The block as claimed in claim 1, where the label material is a metal for X-ray microanalysis, a fluorescent material, or a reactive compound, for reaction with a radioactive isotope.

5. The block as claimed in claim 1, wherein the label layers are substantially parallel and substantially flat, and non-label layers are interposed between the label layers.

6. The block as claimed in claim 1, wherein there are present from 3 to 20 label layers containing different known concentrations of label material.

7. A standard for analysis comprising a uniform section sliced from a block of polymeric material, the section including at least two label layers, each label layer being of uniform thickness and containing a known concentration of a label material uniformly distributed therein.

8. The standard as claimed in claim 7, wherein the area of section is from 0.001 cm$^2$ to 10 cm$^2$.

9. The standard as claimed in claim 7, wherein tne label material is a radioactive isotope.

10. The block as claimed in claim 7, wherein the radioactive isotope is 3-H or 14-C.

11. The block as claimed in claim 7, where the label material is a metal for X-ray microanalysis, a fluorescent material, or a reactive compound for reaction with a radioactive isotope.

12. The blcok as claimed in claim 7, wherein the label layers are substantially parallel and substantially flat, and non-label layers are interposed between the label layers.

13. The block as claimed in claim 7, wherein each label layer contains a different concentration of label material.

14. The block as claimed in claim 7, wherein there are present from 3 to 20 label layers containing different known concentrations of label material.

* * * * *

UNITED STATES PATENT AND TRADEMARK OFFICE
CERTIFICATE OF CORRECTION

PATENT NO. : 4,715,988
DATED : December 29, 1987
INVENTOR(S) : Colin David BELL

It is certified that error appears in the above-identified patent and that said Letters Patent is hereby corrected as shown below:

Title page:

Please change the inventor's name as follows:

Change "David Colin" in item [75] to "Colin David Bell".

Signed and Sealed this

Fourth Day of October, 1988

Attest:

DONALD J. QUIGG

*Attesting Officer*　　　*Commissioner of Patents and Trademarks*